United States Patent [19]

Herweck et al.

[11] Patent Number: 5,782,789
[45] Date of Patent: Jul. 21, 1998

[54] MACROCHANNEL PHOSTHETIC/DELIVERY PATCH

[75] Inventors: Steve A. Herweck, Nashua; Theodore Karwoski, Hollis, both of N.H.

[73] Assignee: Atrium Medical Corporation, Hudson, N.H.

[21] Appl. No.: 325,787

[22] Filed: Oct. 19, 1994

[51] Int. Cl.$^6$ .................................................. A61F 13/00
[52] U.S. Cl. ............................ 602/52; 424/443; 424/444; 424/448; 424/449; 623/1
[58] Field of Search ............................ 428/158, 159; 424/443, 444, 448, 449; 602/52; 623/1

[56] References Cited

U.S. PATENT DOCUMENTS

| | | | |
|---|---|---|---|
| 4,304,010 | 12/1981 | Mano | 606/230 |
| 4,306,318 | 12/1981 | Mano et al. | 623/1 |
| 4,321,711 | 3/1982 | Mano | 606/230 |
| 4,332,035 | 6/1982 | Mano | 606/230 |
| 4,612,337 | 9/1986 | Fox et al. | 604/265 |
| 4,713,070 | 12/1987 | Mano | 623/1 |
| 4,973,609 | 11/1990 | Browne | 521/81 |
| 5,024,671 | 6/1991 | Tu et al. | 623/1 |
| 5,061,276 | 10/1991 | Tu et al. | 623/1 |
| 5,192,310 | 3/1993 | Herweck et al. | 623/1 |
| 5,197,976 | 3/1993 | Herweck et al. | 623/1 |
| 5,258,014 | 11/1993 | Harada et al. | 606/228 |
| 5,411,550 | 5/1995 | Herweck et al. | 623/1 |
| 5,433,909 | 7/1995 | Martakos et al. | 264/209.1 |

FOREIGN PATENT DOCUMENTS 230635  8/1987  European Pat. Off. .
WO 93/21859  11/1993  WIPO .
WO 93/21902  11/1993  WIPO .

OTHER PUBLICATIONS

Langer, Robert, (1990) "New Methods of Drug Delivery". *Science*, vol. 249, pp. 1527–1533.

*Primary Examiner*—Veronica P. Hoke
*Attorney, Agent, or Firm*—Lahive & Cockfield, LLP

[57] ABSTRACT

A prosthetic tissue patch includes a sheet of material having first and second sides, with a plurality of macrochannels extending parallel to each other in the plane of the sheet, and defining a dispersed set of chambers that serves as a reservoir of pharmaceutical material or living culture. The channels communicate through pores in the thin surrounding wall with a surface of the sheet which is placed in contact with tissue and may intergrow therewith. The sheet is preferably 0.2–2.0 mm. thick, with the macrochannels each having a diameter between about 0.1 and 1.5 mm, generally no more than about three quarters of the sheet thickness. A preferred embodiment is formed of polytetrafluoroethylene (PTFE) with an anisotropic porosity structure of nodes which may be oriented generally transverse to the plane of the sheet. The channels are initially filled either by conventional methods, or by insertion of solid filaments of material, and may be capped closed by a special plug. They may be refilled by capillary or pressure connection to a special resupply manifold. The patch performs passive drug delivery, or in vivo culture for active manufacture and topical delivery of bioactive material. The patch also may support growth of natural tissue and become incorporated in the adjacent organ or tissue to which it is attached, or it may serve as a "nursery" for culturing autologous cells to be used elsewhere or in a subsequent operation.

15 Claims, 4 Drawing Sheets

MACROCHANNEL PHOSTHETIC/DELIVERY PATCH

BACKGROUND OF THE INVENTION

The present invention relates to devices for delivering drugs or other bioactive materials to a patient. A number of devices of this general class have recently been developed for particular applications, such as for delivering a drug to inhibit the desire to smoke, or a drug to prevent sea sickness. One such device employs a porous material which attaches to the skin and has a surface through which a drug is absorbed into the body at a slow rate. In addition, mechanical constructions have long existed in which a reservoir or pump is implanted under the skin with a catheter for accessing a blood vessel to deliver drugs directly into the bloodstream. A number of other approaches have been proposed. The present invention is also related to applicants' earlier United States patent applications, the substance of which is included in their International Patent Application PCT/U.S. 92/07828, published on Apr. 1, 1993 as WO93/05730. That application is directed to tubing that is preferably made of expanded polytetrafluoroethylene (PTFE) for use as vascular graft or prosthetic material, in which parallel lumens extending in the tube convey drugs or other bioactive material directly to the bloodstream by permeation through the tube wall. The PTFE material has a high degree of biocompatibility, and has been shown to be capable of supporting tissue ingrowth when used as a vascular implant. The porosity of the material can be controlled such that the polymer material forms an inert and biocompatible network that serves as a scaffold for natural cell growth processes; the preferred porosity extends fairly directly through the walls separating the lumens, and has a size which permits tissue and microvessels to grow deeply into the walls.

In addition to the foregoing constructions, there are known in the art a number of artificial skin or tissue reinforcement materials, which may be used in surgery to cover a trauma site and aid in the regeneration of tissue. Such materials may include tissue harvested from people or other animals which has been specially processed to render it biocompatible and resorbable. In general, such patch material serves as a temporary surface layer to strengthen and protect the healing site. When medication or other bioactive material is to be delivered to the site, the patch may be soaked in appropriate solutions, as is often done, for example, to prepare vascular graft material. To applicants' knowledge, however, no soaking techniques have been developed that are capable of providing a delivery system for precise or extended dosages of material, but rather, soaking addresses, on an interim basis, problems of tissue compatibility, sepsis, clotting or the like.

Accordingly, it is desirable to provide a tissue patch that is not prone to antigenic rejection mechanisms, and having stable, precise and controlled permeation and drug delivery characteristics.

SUMMARY OF THE INVENTION

In accordance with the present invention, a tissue patch includes a sheet of porous polymer material wherein the porosity is preferably determined by a microstructure of nodes and fibrils, and the sheet has a number of tunnels of vastly greater dimension than the pores, extending in the plane of the sheet and preferably parallel to each other, the tunnels constituting chambers for holding bioactive material. The porosity of the material allows fluid communication between the tunnels and one or both surfaces of the patch, while in general any cells or foreign particles are constrained from passing into or out of the tunnels.

In a preferred embodiment, the patch is formed as an extruded sheet of polytetrafluoroethylene (PTFE) having a thickness between approximately 0.2 and 2.0 millimeters, preferably 0.4 to 1.0 millimeters, and having a porosity such that body fluids may permeate entirely into the sheet from at least a first side of the device, when the sheet is in its initial state before tissue growth has occurred. At least the first side of the device is flat, and in a basic embodiment, both sides are flat, whereas the central region between surfaces is spanned by macrotunnel openings in the otherwise continuous sheet. The macrotunnels extend in the sheet parallel to each other and spaced apart by a distance preferably somewhat greater than the thickness of the device, each tunnel having a diameter between approximately two-tenths and nine-tenths of the sheet thickness, so as to occupy a substantial portion of the volume between the external surfaces of the sheet. In another embodiment, one surface is flat while an opposite surface is corrugated or undulating, to form a regular sequence of peaks or ridges alternating with dips or valleys. The macrotunnels extend directly under and parallel to each ridge of the sheet. In this embodiment, the tunnels may have a somewhat larger absolute or relative diameter, which may even be greater than the minimum thickness of the sheet, and the volumetric capacity of the tunnels is increased while the overall mass of the PTFE sheet structure remains small in relation to its large exposed surface area and to its interior volume. In a further embodiment of either of these two constructions, the sheet may be formed of an expanded, porous, or sponge-like biocompatible polymer, or of a copolymer, for example made of a polyurethane and a PTFE, to achieve particular physical properties, such as enhanced elasticity or tensile strength, chemical compatibility, and the like.

Preferably, however, all or a substantial portion of the material, is PTFE, and the patch is given a defined pore structure, after manufacture as a multi-channeled sheet, by stretching the sheet to in a controlled manner introduce the aforesaid porosity, e.g., a microstructure of nodes and fibrils. In a most preferred embodiment of this aspect of the invention, rather than micron-scale nodes, the nodes are made to extend entirely from the wall of each channel to an adjacent surface of the sheet, so that the space between adjacent nodes defines a confined but directed path for permeation of liquids or gases outwardly to the surface of the sheet. Different porosities may be provided above and below the channels, so that permeation is enhanced to the "active" or tissue-contacting side, and inhibited on the outer or unattached side. On the active side of the preferred PTFE patch, each intra-node diffusion path is a fissure-shaped opening crossed by fibrils, which effectively block transit by cells, although, as noted above, the fibril-filled spaces are amenable to the slower processes of tissue ingrowth, and also to large molecule diffusion or transport. This allows the patch to slowly become incorporated into the tissue to which it is attached, while it operates as a barrier to mobile cells or particulate material. This form of porous barrier which blocks cell travel but not tissue ingrowth is intended to prevent occurrence of short-term and cell-mediated immune responses or tissue rejection.

BRIEF DESCRIPTION OF THE DRAWINGS

These and other features of the invention will be understood by reference to the following description, taken together with illustrations of representative embodiments, wherein.

DETAILED DESCRIPTION

Figure 1:
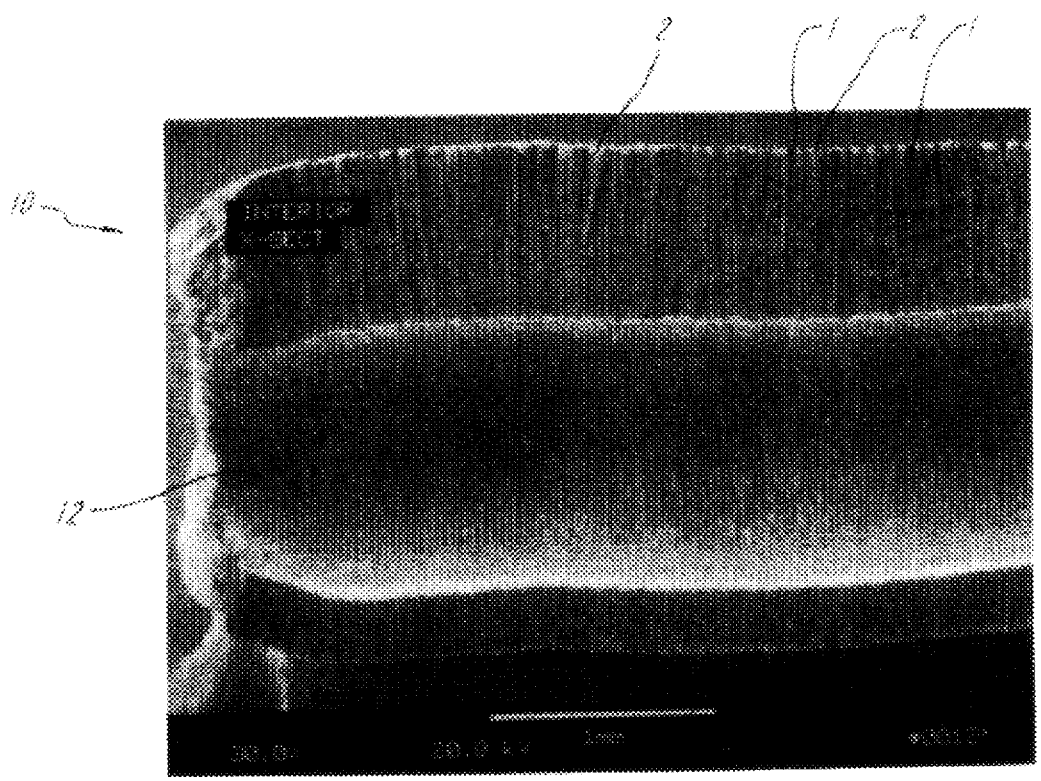
FIG. 1 shows an electron micrograph of PTFE material useful in the practice of the present invention taken along the section illustrated in FIG. 2.

FIG. 1 shows an electron micrograph of polytetrafluoroethylene material which has been fabricated to provide a porous structure for implantation in the human body. In the discussion of polytetrafluoroethylene porosity, the term "pore" is used in a non-pictorial sense, by way of analogy only, to describe a relative degree of openness of the apparently solid material. Depending upon particular usages involved, different measures of porosity may be employed. For example, it is common to describe porosity in terms of the ethanol bubble point; or the rate of gas permeation through a membrane or solid at a particular pressure; or the relative density compared to the densest possible state of the material involved. Other measures of porosity are possible. It is also common, in the context of filtration properties, to define porosity by reference to a fictitious "pore size" which may be determined by reference to a largest or mean particle size which passes the filter, or by reference to the level of filtration achieved by a standard filter material of known pore size. Thus, the term porosity is a highly variable one. However, as used herein, the term is understood to encompass those measures of porosity customarily used to describe graft and prosthetic materials and devices of PTFE, and where more particular meanings are intended, the configuration of the PTFE node/fibril microstructure will be discussed.

As shown in FIG. 1, the pore structure of a material such as expanded PTFE consists of a microstructure having a generally fragmented appearance in which larger relatively solid "nodes" 1 of material are held together by less substantial and more numerous "fibrils" 2 of the material that cross or criss-cross the space between nodes. IThe particular material shown in the photograph, FIG. 1, is expanded PTFE formed by a process of compressing PTFE fine powder with a lubricant and extruding it through a extrusion nozzle at very high pressures. The extruded product is baked dry to removed solvent, and is then stretched in one or more directions, for example, by pulling it, subjecting it to an inside-to-outside pressure differential, or placing it in a frame or device that exerts mechanical tension in one or more directions. The stretching operation may extend or expand the article by a factor between two and one thousand, with the particular example shown being expanded by a factor of approximately four. Heat is usually then applied in a sintering step to fix the dimensions of the article in the expanded state and enhance the strength of the product.

As shown, the expansion introduces a general fracturing of the plastic material on a microscopic level which is responsible for its property of porosity. In the case of PTFE, the porous product has been found especially useful for surgical applications, since it is essentially biologically inert and the fibrils are of such a small diameter, for example, 10–100 angstroms, that cellular material may simply bend the fibers and grow into spaces therebetween. The PTFE when prepared with a proper porous microstructure may thus serve as an immobilizing scaffold or frame about which cellular regeneration may take place. With the porous microstructure illustrated in FIG. 1, not only can tissue grow into the spaces, but capillary blood vessels and other differentiated tissue may form.

This high degree of biocompatability of PTFE material, however, stems in part from its fluorinated bonds which are essentially inert and hydrophobic. Thus, the use of PTFE pads or articles to constitute a drug delivery system is complicated by the fact that most drugs and other materials do not adhere well to a PTFE surface. In practice, this has required that the surface chemistry of implanted PTFE articles be modified by special plasma, heat, chemical or etching treatments to introduce surface texture or functionality that enables biological material to bond to or be securely held by the PTFE substrate.

Figure 2:
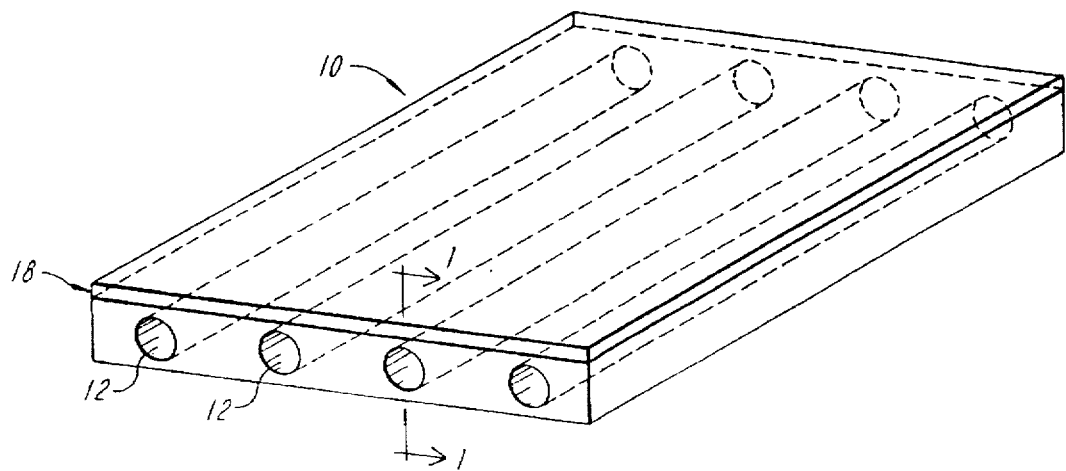
FIG. 2 shows a first embodiment of the invention.

FIG. 2 shows, in schematic illustration, a perspective view of a basic embodiment 10 of the present invention. As shown, article 10 is a sheet of porous material having tunnels 12 extending therethrough. The tunnels extend in the plane of the sheet and are parallel to each other, and are spaced between roughly one-half and five times the thickness of the sheet apart from each other, so that they form a regular array over a substantial region of the sheet. Optionally, one surface of the sheet, illustratively the top, has a further layer 18 which may, for example, be non-porous, and preferably both non-porous and resorbable, to seal or temporarily seal one side of the patch. This preferentially places the other side of the patch in diffusion-mediated fluid communication with the tunnels 12.

Returning briefly to FIG. 1, the particular specimen shown in that Figure represents a presently preferred porous microstructure of a PTFE material which is obtainable wherein the extruded PTFE material has been stretched in a direction extending along the axis of channels 12. This single-axis stretch results in a node and fibril microstructure wherein the nodes take the form of thin plates lying generally normal to the stretch axis, with adjacent plates interconnected by fibrils lying generally parallel to the stretch axis. The spaces between adjacent nodes, shaped like deep fissures, thus define channels which are crossed by the fibrils. The channels may be conceptually understood as growth or transport paths through the wall, while the fibrils further define the overall porosity as well as serving as flexible network to accommodate cells growing in those paths. By arranging that the mean axial node spacing is between twenty and eighty micrometers, and most preferably about sixty micrometers, on the tissue-contacting side, cell ingrowth and vascularization of the PTFE wall is encouraged.

In use, the tunnels 12 of the patch are filled with an appropriate bioactive material and the patch is surgically attached, e.g., by suturing, stapling or by gluing with a cryoglobin glue, to an exposed vascularized tissue site. Material stored in the tunnels then permeates to the adjacent tissue. For this application, the patch material is made porous by fabricating it with a stretching step to develop an internode spacing of between approximately one micron and several hundred microns, preferably about fifty microns, although the precise porosity will depend on factors such as the solubility, viscosity and other properties of the bioactive material which is to be loaded into the tunnels 12, as well as on the tissue growth characteristics of the intended attachment site. For example, if the bioactive material is highly soluble, smaller pores will be necessary to control the rate of permeation. Similarly, if the tissue at the intended site of tissue attachment is highly proliferating and it is desired to inhibit cellular ingrowth, then pore sizes should also be kept small, under several microns. While the generic term "pore size" has been used, it is understood that, more accurately to achieve such small pore size, the node spacing (distance between adjacent nodes) and the fibril length should each be controlled so that they present the desired porosity. For pore sizes below several micrometers, this generally requires that the node spacing and fibril length each be under about ten or twenty micrometers. As discussed further below, the rate of permeation may also be controlled by varying the thickness of the channel walls. However, in general, the total thickness as indicated above is preferably thin, under one or two millimeters, and a certain minimum thickness of 0.2–0.3 millimeters may be necessary for structural integrity, so thickness variation alone may not provide a great range of control over the perfusion rate.

By way of representative dimensions, the thickness of the patch is approximately one millimeter, while the diameter of the channels is typically between about two-tenths and nine-tenths of the thickness. The spacing between channels is between about one-tenth and five times the sheet thickness. These limits are representative only, the exact delivery characteristics achieved with any one set of dimensions being subject to empirical measurement and characterization; however, the intent is to provide a strong tissue or web, of which between five and ninety-five percent by volume (not counting the "pores") of the sheet consists of a discrete array of open material-storing channels. In particular applications, the porosity is tailored so that the tissue to which it is attached may grow into and through the web; in that case, the web, if implanted, becomes a harmless artifact or even a therapeutic prosthesis, a tissue-strengthening, tissue-replacing or tissue repair patch, once its contents have been delivered.

As discussed further below, the patch may also be configured for remote filling, or refilling of its macrochannel reservoir, so that relatively larger doses of material may be continuously supplied or intermittently replenished. Before describing such system, however, variations of the simple extruded sheet of FIG. 2 will be considered.

Figure 3:
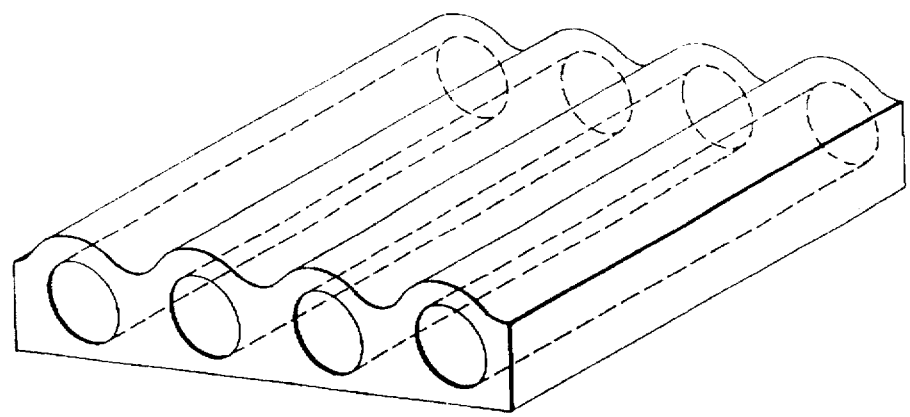
FIG. 3 shows a second embodiment of the invention.

FIG. 3 shows a second embodiment of the device. In this embodiment, the top surface is ridged, or corrugated, with corrugations or peaks 22 overlying the linearly extending tunnels 12. The advantage of this embodiment is simply that it provides a greater top to bottom dimension of the sheet, so that the tunnels in the interior are enlarged relative to the average sheet thickness, while it maintains a wall of sufficient integrity that does not become excessively thin and has greater strength surrounding the reservoirs formed therein.

One method of making a macrochannel patch of the invention having the above-described characteristics is to form it by extrusion, for example from a paste, which is made to flow at high pressure along a path through an extrusion opening having a shape corresponding to the desired cross-section. Suitable pastes are mixed from a mineral solvent, such as ISOPAR, and a dry PTFE powder, which is available from any of several suppliers.

Figure 4:
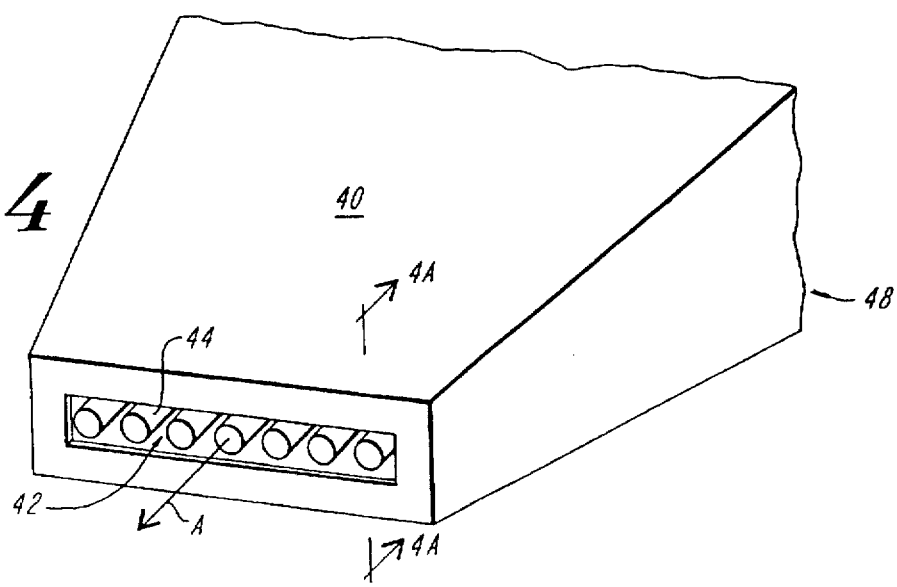
FIGS. 4 and 4A show perspective and sectional views of an extrusion head for manufacturing the embodiment of FIG. 2.
Figure 4A:
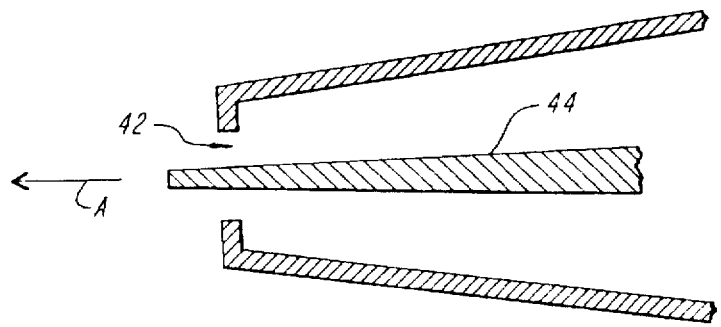

FIGS. 4 and 4A show front and sectional views through a suitable extrusion die for forming the patch material of FIG. 2. Arrow "A" indicates the direction of extrusion and corresponds to the axis of the tunnels 12 in the extruded sheet of FIGS. 2 and 3. As shown, the die 40 has a broad thin outlet 42 with a height t, illustratively 0.5–2.0 mm in height, and a plurality of pins 44 extending through the opening oriented along the extrusion axis A. Pins 44 taper, as does the extrusion head as a whole, so that the infeed area 48 of the head 40 is many times greater than the area of the extrusion opening 42. In general, the long taper serves to define a high pressure laminar flow path toward opening 42, and during the course of flow along this path the relatively long PTFE molecules achieve some degree of mutual alignment and are brought into close proximity with each other, so that the final extruded sheet has a relatively high tensile strength, and can be stretched to have highly regular directional porous microstructure. In particular, as noted above, stretching along the axis "A" of the tunnels may produce nodes shaped like thin flat scales or plates oriented across the plane of the sheet, with an open network of fibrils filling the spaces between nodes and extending parallel to the in-plane direction.

As the sheet is extruded, the parallel macrochannels or tunnels 12 are formed at locations of the tapered channel-forming pins 44 in the extrusion opening 42. The channels and pins are each illustrated as having a round cross-section, but may be oval, more or less rectangular or of other aspect. What is important is that they define relatively large tunnels or chambers extending continuously inside the thin sheet of patch material, in which a continuous mass of material may be deposited for permeation in a direction transverse to the tunnels to adjacent surfaces of the patch. Reference is hereby made to applicants' copending U.S. patent application Ser. No. 08/031,238, filed Mar. 12, 1993 now U.S. Pat. No. 5,433,909 for a discussion of representative extrusion techniques and recipes for extrusion materials to form such a sheet. The contents of that application are hereby incorporated by reference herein. It will be understood that while that patent application describes the extrusion of tubular material for forming vascular grafts, a flat patch may be made from such a tube by slitting the tube lengthwise. Applicant hereby incorporates herein by reference applicants' other above-noted prior U.S. patent applications and issued patents dealing with extruded multilumenal devices, that is, devices having one or more lumena extending parallel to a primary lumen within the bounding wall of an extruded article of PTFE material. Those patent applications show representative extrusion dies for forming cylindrical preforms having parallel tubular channels formed within their walls and extending along their axis. Most of these multi-lumenal articles, if slit lengthwise, would yield a flat sheet with at least one channel extending in the plane of the sheet. It will be understood, however, that the present invention is not limited to sheet material produced by slitting extruded tube structures, but includes biocompatible porous sheet material produced by other methods, or extruded directly as a flat sheet from a sheet extrusion die as illustrated in FIGS. 4 and 4A, or assembled from sheet and tube stock as described below.

Several aspects of the extrusion techniques of the aforesaid patent applications merit discussion as methods of making sheet material having macrochannels in accordance with the present invention.

Returning again to FIG. 1, that photograph shows an axially-extending cross-sectional view along one macrochannel 12 of sheet structure made by extrusion. As shown, the sheet thickness is approximately 2.2 millimeters, with a 1.15 mm diameter macrochannel running through the sheet. The upper wall is 0.7 mm thick and the lower wall is 0.3 mm thick, the lower wall thus providing a more direct diffusion route to or from the channel and the lower surface. The extrusion is formed of PTFE, made as described in the aforesaid U.S. Pat. No. 5,433,909, and the sheet is rendered porous by post-extrusion stretching directed along the axis of the macrochannel; this stretching produces flat node bodies 15, visible as dark lines in the Figure. These nodes 15, or solid globs of material in the porous microstructure, are oriented in flat plates extending normal to the surface of the sheet, so that the spaces between adjacent nodes run directly from the macrochannel 12 to the nearest (upper or lower) surface. These fissure-shaped internodal spaces are crossed by a great number of fine fibrils approximately five to fifty microns long, which are oriented generally along the axis, i.e., parallel to the surface. The fibrils prevent passage of particles, and slow the rate of diffusion of fluids and large molecules, so that despite the apparently coarse nodal structure, the structure exhibits a relatively fine pore size as measured, for example, by accepted ANSI testing techniques.

In accordance with this further aspect of the invention, porosity is controlled such that a first side of the sheet, illustratively the bottom in the figures above, is intended for bearing directly against tissue and has a pore size adapted for supporting cellular growth at its contact surface. This leads to an intimate contact, and actually amounts to incorporation or intergrowth of the sheet to the tissue, which for various tissue types allows capillaries to grow into the sheet to enhance the efficiency of material transport or delivery. The opposite side of the sheet facing away from the tissue preferably has a smaller pore size, for example, below approximately several microns. The smaller pores inhibit permeation or outflow of material in that direction, so that material residing in the macrochannel is effectively delivered only to the underlying contiguous tissue. The provision of different porosities on the two sides of a sheet may be achieved by introducing variations in the ISOPAR solvent or carrier concentration in the paste used for extrusion, as described in the aforesaid U.S. Pat. No. 5,433,909. For example, the sheet may be extruded from a billet preform having two layers of differently-lubed PTFE material as described therein, or having several layers of different PTFE materials as described in U.S. Pat. No. 4,973,609. Other methods of achieving different porosity on one side may be used, such as heating, calandering, or coating one side, provided these postextrusion thermal or mechanical operations are performed with sufficient control to avoid closing off the macrochannels.

The non-natural synthetic polymer PTFE is hydrophobic, and, as observed above, does not readily hold or adhere to commonly encountered biological materials. The macrochannels 12 are intended to overcome this limitation by forming chambers for physically holding a discrete supply of material within the body of the sheet 10. As discussed above, these chambers may amount to fifty percent or more of the total volume between the two faces of the patch sheet, and may be easily filled.

Figure 6:
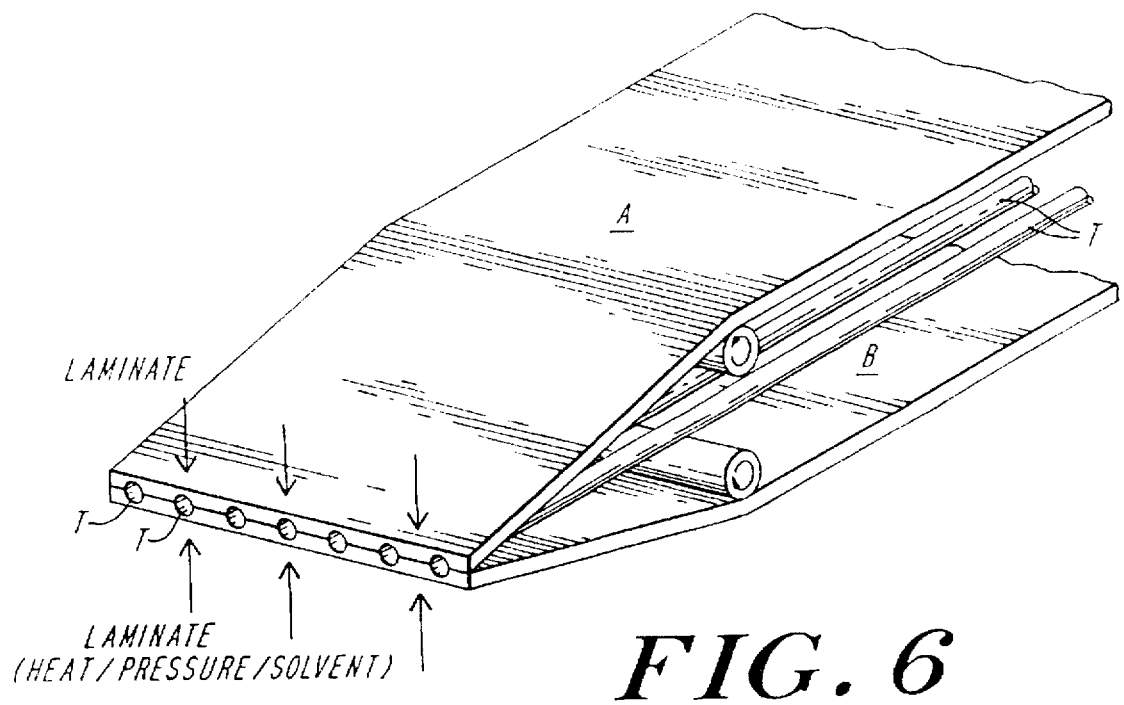
FIG. 6 shows an alternative method of manufacture.

FIG. 6 illustrates another method of forming the multi-tunnel patch of the present invention. In this method, first and second sheets of material, A and B are placed above and below a set of parallel porous tubes T, and the composite structure is unitized, for example continuously laminated together by solvent, heat, pressure or some non-destructive combination of these techniques, to form a sheet with included tunnels. In this case, permeation characteristics may be determined by the porosity and thickness of the tubes T and lower sheet B.

The invention further contemplates patches wherein means are provided for sealing the ends of macrochannels, and wherein means are provided for refilling the macrochannels. Sealing may be readily accomplished by welding a seam transverse to the axis of the channels using heat, ultrasonic energy or the like. More generally, the channel may be both closed off, and refilled using a specifically-configured connector manifold that connects to an external or a subdermal medication reservoir, a refill tube, pump or other delivery system of conventional type.

Figure 5:
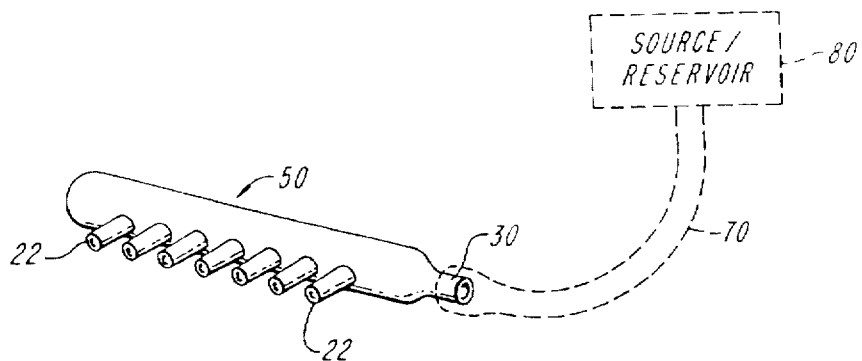
FIG. 5 shows a plug or manifold for use with the inventions of FIGS. 2 and 3.

Such an arrangement is shown in FIG. 5, wherein a manifold 50 has a plurality of connector nozzles 22, each communicating with a central chamber or passage defined within the manifold, the manifold 50 in effect being structurally similar to an array of medical tubing connectors, fabricated of biocompatible material, extending from a single block or body, and having a greatly reduced size to so as to connect to and to fit within the tunnels 12 of the patch 10. Manifold 50 is formed with a hollow tube connector 30, preferably located at one end or side thereof, that connects the common delivery passage formed by the manifold body to a catheter 70 shown in phantom, so that fluid communication is established with a reservoir or pump mechanism 80, which, in turn, may be either implanted or external. Alternatively, a similarly shaped member may be formed as a solid body of polymer, to act simply as a multi-plug array for closing the ends of the tunnels or macrochannels 12 once they have been filled. In that case, the nozzles 22 are replaced by a plurality of equi-spaced solid stub plugs.

For the basic patch 10, filling of the sheet may be initially accomplished using a small gauge hypodermic needle to fill each channel with a liquid preparation. Alternatively, drug material may be compounded in a solid bioresorbable base matrix and formed into a solid strand of material, which can then be cut to length and threaded into the open macrochannels. In this case, the diameter and solubility of the strand are primary determinants of the drug delivery rate, while the strand volume determines the total dose.

Thus the patch is configured as a temporary dispenser of medication or a refillable one, depending in part upon the intended use.

Figure 5A:
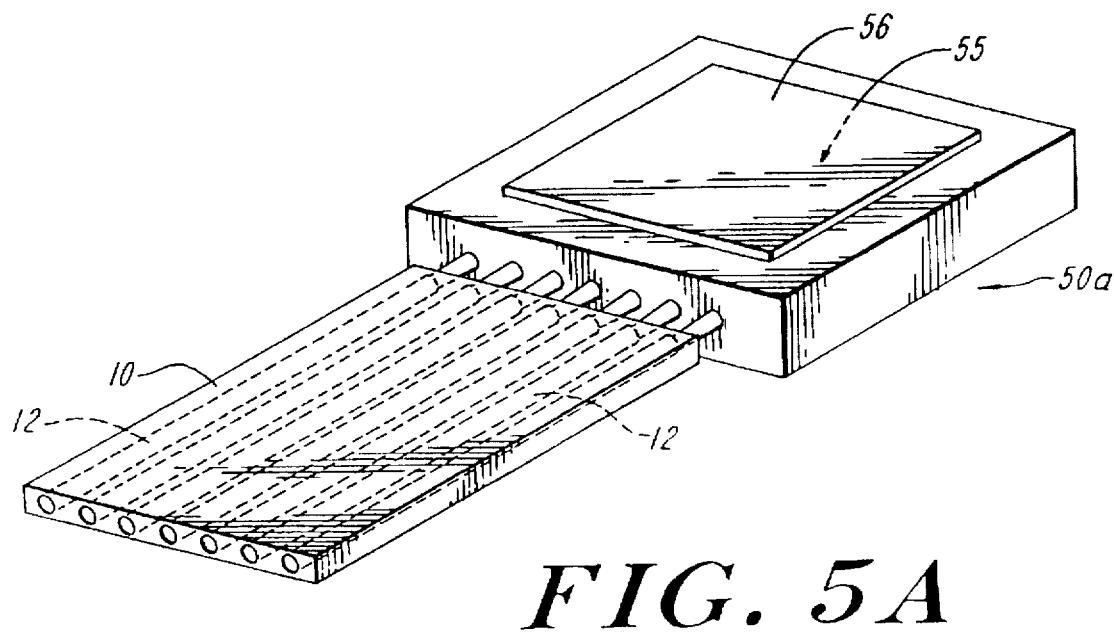
FIG. 5A shows a reservoir for attachment to the embodiment of FIGS. 2 or 3.

Another embodiment of an end cap or plug 50a is shown in FIG. 5A. In this embodiment, an internal reservoir 55 provides a self-contained material source directly attached to the patch 10 to fill its macrochannels. Reservoir 55 may itself be refilled transdermally by injecting material with a hypodermic needle through a broad flat permeable and resealable septum 56. The reservoir may be overfilled to a positive pressure, so that its contents are driven by pressure into the macrochannels, or may be filled with appropriate salts, solutions or other forms of a desired bioactive material to achieve a delivery rate controlled by osmotic pressure.

The invention also contemplates that in addition to drugs or nutrient media, patch 10 may be used to hold foreign cellular material and deliver products of cellular activity to the patient's adjacent body tissue. In this case the macrochannels 12 may be filled with cell culture material which lives and is cultured in situ to produce the desired products. For example, cells that produce an enzyme or other bioactive material may be initially loaded into the macrochannels with appropriate culture and support media. The patch is then attached to an organ or implanted in a location where the body continues to provide or supplement the necessary nutrients or support materials in its extracellular environment, so the culture cells remain supported and they continue to grow and be nutured by the patient's fluids and metabolic processes in vivo, while generating their own characteristic cellular products. These products diffuse across the broad, flat surface of the patch 10 into adjoining tissue (not shown), and the vasculature and extracellular fluid of the adjoining tissue serve to wash the environment and bring nutrient materials to the growing cell culture as well as receive its essential proteins or other biochemical products. In this aspect, the patch thus serves as an artificial stratum or fascia interposed in an appropriate cellular and metabolic environment to nurture cell growth. As a specific example, islet of Lagerhans cells may be seeded in the tunnels 12 and the graft material attached to an otherwise healthy and culture-compatible site to introduce insulin into a patient's blood stream and supplement the patient's subnormal insulin production. In a like manner, the tunnels may be filled with solid or liquid bioactive but non-living material. In that case, the mechanism of delivery is one of ongoing solvation and diffusion of fluid across the tissue patch wall, in and out of the macrochannels. Notably, when this technique is applied to foreign cells or cellular products placed in the macrochannels, the surrounding wall structure serves to isolate the material in the channels from a cell-mediated immune response, since the foreign cells cannot escape, and the patient's own large cells, e.g. leukocytes and immunity-mediating blood cell types, also cannot physically travel through the porous material.

It will be seen that the invention provides a novel delivery system having a reservoir of treatment material disposed in a thin array of extended pockets or tunnels inside a flat sheet over a broad area, the sheet wall defining a containment or isolation barrier through which direct fluid exchange occurs. In various applications, it provides for broad area controlled diffusion of a drug into tissue, or different types of patching, repair or metabolic remediation of tissue by incorporating material or growing cells directly adjacent to or intergrown with affected tissue.

While the invention has been described with reference to a PTFE material and preferred methods of forming chamber and pore structures in that material, such description is by way of illustration only and the invention may be modified to provide a full range of culture or treatment conditions by incorporating other materials and introducing other forms of anisotropic or symmetrical pore microstructures. Among other polymers which may advantageously be employed, polyurethane may be expanded by techniques known in the art, and copolymers of polyurethane and PTFE may be used in order to provide a sheet structure having enhanced strength properties with much of the porosity and biocompatibility properties of PTFE. Other fluorinated polymers may also be used.

The invention being thus disclosed, variations and modifications will occur to those skilled in the art and all such variations are intended to be within the scope of the invention as set forth in the claims appended hereto.

What is claimed is:

1. A non-tubular shaped patch of about one to three millimeters thickness comprising a porous sheet of biocompatible material selected from the group consisting of a fluorinated polymer and a polyurethane having a thickness with a plurality of channels formed therein, the channels being distinct chambers surrounded by porous material of said sheet and the channels each wholly extending along an axis lying in a plane of said sheet parallel to each other form a planar array of holding chambers in said sheet, and bioactive material disposed in said channels, the channels having a diameter between about one-fourth and three-fourths of said sheet thickness effective to contain a substantial volume of material for permeation through said porous sheet to a surface thereof.

2. A patch according to claim 1, wherein the sheet has a thickness t and the channels have a cross-sectional dimension transverse to said axis of between approximately 0.1 and 0.9 t.

3. A patch according to claim 1, wherein the sheet has a thickness under approximately two millimeters.

4. A patch according to claim 1, wherein the channels extend parallel to each other at a spacing from each other comparable to the thickness of the sheet.

5. A patch according to claim 1, wherein the sheet includes a first surface and a second surface opposed to the first surface, and the sheet has an anisotropic pore structure which is different on said first surface from said second surface such that material is selectively delivered through said pores to said first surface.

6. A patch according to claim 1, wherein some but not all said channels contain material for delivery to tissue and a rate of delivery to tissue is proportional to the number of tunnels containing material.

7. A patch according to claim 1, further comprising adhesive means on one of said first or second surfaces of said sheet for securing the sheet to tissue.

8. A patch according to claim 7, wherein said sheet further includes bioactive material distributed in pores of the sheet.

9. A patch according to claim 8, wherein the adhesive means is a temporary adhesive for temporarily securing the sheet to tissue pending ingrowth of tissue into the sheet.

10. A patch according to claim 1, wherein the sheet has a substantially flat surface for contracting tissue, and a non-flat surface opposed thereto having a plurality of raised regions wherein the channels are formed beneath the raised regions.

11. A patch according to claim 10, wherein the raised regions provide walls of substantially uniform thickness over the channels.

12. A patch according to claim 5, where in said first surface has a porosity greater than porosity of said second surface.

13. A patch according to claim 1, wherein the channels are spaced apart by a distance between approximately one and five times said sheet thickness.

14. A patch according to claim 1, wherein said bioactive material is a solid strand which is fitted in at least one of said channels.

15. A method of providing material to a region of body tissue, such method comprising the steps of providing a non-tubular shaped patch sheet of porous biocompatible material selected from the group consisting of a fluorinated polymer and a polyurethane, the sheet having an inner and an outer surface with a thickness of more than about one and under approximately three millimeters and a plurality of channels formed in said sheet for receiving a bioactive material, the channels each wholly extending along an axis in the plane of and interior to the sheet, all channels being parallel to each other and to one surface of the sheet providing a bioactive material in said channels, and attaching said one surface of the sheet to the region of body tissue so that the bioactive material permeates from the channels through said porous material across said one surface into said region.

* * * * *

UNITED STATES PATENT AND TRADEMARK OFFICE
CERTIFICATE OF CORRECTION

PATENT NO. : 5,782,789
DATED : July 21, 1998
INVENTOR(S) : Steve A. Herweck, Nashua; Theodore Karwoski, Hollis, both of N.H.

It is certified that error appears in the above-indentified patent and that said Letters Patent is hereby corrected as shown below:

On the Title page, item [54] and in column 1, lines 1 and 2:

The second word of the title <u>incorrectly</u> reads:

PHOSTHETIC/DELIVERY

Change the spelling to:

PROSTHETIC/DELIVERY

Therefore, the entire "corrected" title should read:

MACROCHANNEL PROSTHETIC/DELIVERY PATCH

Signed and Sealed this

Twenty-fourth Day of November, 1998

Attest:

BRUCE LEHMAN

*Attesting Officer*  *Commissioner of Patents and Trademarks*